US008204606B2

(12) United States Patent
Zhang et al.

(10) Patent No.: US 8,204,606 B2
(45) Date of Patent: *Jun. 19, 2012

(54) IMPLANTABLE LEAD FOR SEPTAL PLACEMENT OF PACING ELECTRODES

(75) Inventors: Yongxing Zhang, Little Canada, MN (US); James O. Gilkerson, Stillwater, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 913 days.

This patent is subject to a terminal disclaimer.

(21) Appl. No.: 12/144,247

(22) Filed: Jun. 23, 2008

(65) Prior Publication Data

US 2008/0262586 A1  Oct. 23, 2008

Related U.S. Application Data

(63) Continuation of application No. 10/325,433, filed on Dec. 19, 2002, now Pat. No. 7,392,094.

(51) Int. Cl.
*A61N 1/05* (2006.01)

(52) U.S. Cl. ....................................... 607/126

(58) Field of Classification Search .................. 607/119, 607/122–126
See application file for complete search history.

(56) References Cited

U.S. PATENT DOCUMENTS

| | | | |
|---|---|---|---|
| 3,209,305 A | 9/1965 | Bruckner et al. | |
| 3,974,834 A | 8/1976 | Kane | |
| 3,995,623 A * | 12/1976 | Blake et al. | 600/381 |
| 4,046,151 A | 9/1977 | Rose | |

(Continued)

FOREIGN PATENT DOCUMENTS

| | | |
|---|---|---|
| JP | 3-168162 | 7/1992 |
| JP | 09-508054 | 8/1997 |
| JP | 2001-522287 | 11/2001 |
| JP | 2002-126095 | 5/2002 |
| WO | WO 96/15665 | 5/1996 |
| WO | WO 98/48896 | 11/1998 |

OTHER PUBLICATIONS

"Servometer Miniature Metal Bellows", http://www.servometer.com/bellows.html, Downloaded from: http://web.archive.org/web/20041016084534/http://www.servometer.com/bello-ws.html, (Oct. 16, 2004 (Archived Copy)), 3 pages.

(Continued)

*Primary Examiner* — George Evanisko
(74) *Attorney, Agent, or Firm* — Faegre Baker Daniels LLP

(57) ABSTRACT

A pacing lead having a lead body configured into a pre-formed J-shape. The lead includes a pacing electrode coupled to an intermediate portion of the lead body and located distally from a bottom of the pre-formed J-shape. The lead is adapted to be placed within a heart in a J-shaped configuration with the electrode positioned proximate a ventricular septum or a right ventricular outflow tract such that at least a portion of the distal end of the lead body is located within a pulmonary artery. In one embodiment, the distal end of the lead is configured to be passively fixated within the pulmonary artery. Another aspect includes a lead body wherein a section of the intermediate portion of the lead body is less stiff than adjacent sections of the lead body. The lead includes a pacing electrode coupled to the intermediate portion of the lead body and located distally from the less stiff section. The lead is adapted to be placed within a heart in a J-shaped configuration with the less stiff section near a bottom of the J-shape such that the electrode is positioned proximate a ventricular septum or a right ventricular outflow tract and at least a portion of the distal end of the lead body is fixated within a pulmonary artery.

6 Claims, 4 Drawing Sheets

U.S. PATENT DOCUMENTS

| | | | |
|---|---|---|---|
| 4,307,928 A | 12/1981 | Petlock, Jr. | |
| 4,332,259 A | 6/1982 | McCorkle, Jr. | |
| 4,402,328 A | 9/1983 | Doring | |
| 4,458,677 A | 7/1984 | McCorkle, Jr. | |
| 4,471,777 A | 9/1984 | McCorkle, Jr. | |
| 4,488,561 A | 12/1984 | Doring | |
| 4,576,162 A | 3/1986 | McCorkle | |
| 4,582,056 A | 4/1986 | McCorkle, Jr. | |
| 4,595,009 A | 6/1986 | Leinders | |
| 4,627,439 A | 12/1986 | Harris | |
| 4,632,125 A * | 12/1986 | Webler et al. | 600/505 |
| 4,641,656 A | 2/1987 | Smits | |
| 4,643,201 A | 2/1987 | Stokes | |
| 4,759,378 A * | 7/1988 | Swendson et al. | 607/122 |
| 4,957,111 A | 9/1990 | Millar | |
| 4,986,270 A | 1/1991 | Cohen | |
| 4,991,603 A | 2/1991 | Cohen et al. | |
| 4,998,975 A | 3/1991 | Cohen et al. | |
| 5,000,190 A * | 3/1991 | Petre | 600/526 |
| 5,014,696 A | 5/1991 | Mehra | |
| 5,029,585 A * | 7/1991 | Lieber et al. | 600/396 |
| 5,044,375 A | 9/1991 | Bach et al. | |
| 5,103,821 A | 4/1992 | King | |
| 5,107,834 A | 4/1992 | Ideker et al. | |
| 5,144,960 A * | 9/1992 | Mehra et al. | 607/125 |
| 5,176,137 A | 1/1993 | Erickson et al. | |
| 5,217,318 A | 6/1993 | Peppel | |
| 5,224,491 A | 7/1993 | Mehra | |
| 5,226,427 A | 7/1993 | Buckberg et al. | |
| 5,246,014 A | 9/1993 | Williams et al. | |
| 5,314,462 A | 5/1994 | Heil et al. | |
| 5,336,252 A | 8/1994 | Cohen | |
| 5,342,413 A | 8/1994 | Hirschberg et al. | |
| 5,353,800 A | 10/1994 | Pohndorf et al. | |
| 5,387,233 A | 2/1995 | Alferness et al. | |
| 5,387,234 A | 2/1995 | Hirschberg | |
| 5,403,351 A | 4/1995 | Saksena | |
| 5,405,374 A | 4/1995 | Stein | |
| 5,409,469 A | 4/1995 | Schaerf | |
| 5,411,527 A | 5/1995 | Alt | |
| 5,423,772 A | 6/1995 | Lurie et al. | |
| 5,423,806 A | 6/1995 | Dale et al. | |
| 5,423,865 A | 6/1995 | Bowald et al. | |
| 5,433,729 A * | 7/1995 | Adams et al. | 607/5 |
| 5,433,742 A | 7/1995 | Willis | |
| 5,447,519 A | 9/1995 | Peterson | |
| 5,476,498 A | 12/1995 | Ayers | |
| 5,476,499 A | 12/1995 | Hirschberg | |
| 5,476,500 A | 12/1995 | Fain et al. | |
| 5,531,779 A | 7/1996 | Dahl et al. | |
| 5,545,204 A | 8/1996 | Cammilli et al. | |
| 5,571,159 A * | 11/1996 | Alt | 607/122 |
| 5,609,621 A | 3/1997 | Bonner | |
| 5,628,779 A | 5/1997 | Bornzin et al. | |
| 5,634,936 A | 6/1997 | Linden et al. | |
| 5,639,276 A | 6/1997 | Weinstock et al. | |
| 5,643,338 A | 7/1997 | Bornzin et al. | |
| 5,643,580 A | 7/1997 | Subramaniam | |
| 5,649,974 A | 7/1997 | Nelson et al. | |
| 5,674,217 A | 10/1997 | Wahlstrom et al. | |
| 5,674,272 A | 10/1997 | Bush et al. | |
| 5,683,447 A | 11/1997 | Bush et al. | |
| 5,693,081 A | 12/1997 | Fain et al. | |
| 5,697,965 A | 12/1997 | Griffin, III | |
| 5,713,867 A | 2/1998 | Morris | |
| 5,728,140 A | 3/1998 | Salo et al. | |
| 5,769,858 A | 6/1998 | Pearson et al. | |
| 5,772,693 A | 6/1998 | Brownlee | |
| 5,788,647 A | 8/1998 | Eggers | |
| 5,800,498 A | 9/1998 | Obino et al. | |
| 5,803,928 A | 9/1998 | Tockman et al. | |
| 5,843,117 A | 12/1998 | Alt et al. | |
| 5,843,141 A | 12/1998 | Bischoff et al. | |
| 5,851,226 A | 12/1998 | Skubitz et al. | |
| 5,861,023 A | 1/1999 | Vachon | |
| 5,871,530 A | 2/1999 | Williams et al. | |
| 5,897,584 A | 4/1999 | Herman | |
| 5,902,331 A | 5/1999 | Bonner et al. | |
| 5,922,014 A | 7/1999 | Warman et al. | |
| 5,925,073 A | 7/1999 | Chastain et al. | |
| 5,932,360 A | 8/1999 | Hazlitt et al. | |
| 5,994,444 A | 11/1999 | Trescony et al. | |
| 6,006,122 A | 12/1999 | Smits | |
| 6,021,354 A | 2/2000 | Warman et al. | |
| 6,038,472 A | 3/2000 | Williams et al. | |
| 6,043,273 A | 3/2000 | Duhaylongsod | |
| 6,055,457 A | 4/2000 | Bonner | |
| 6,076,014 A | 6/2000 | Alt | |
| 6,093,982 A | 7/2000 | Kroll | |
| 6,117,128 A | 9/2000 | Gregory | |
| 6,122,553 A | 9/2000 | Idekar et al. | |
| 6,129,750 A | 10/2000 | Tockman et al. | |
| 6,132,390 A | 10/2000 | Cookston et al. | |
| 6,159,237 A | 12/2000 | Alt et al. | |
| 6,161,029 A | 12/2000 | Spreigl et al. | |
| 6,178,355 B1 | 1/2001 | Williams et al. | |
| 6,223,087 B1 | 4/2001 | Williams | |
| 6,245,064 B1 | 6/2001 | Lesh et al. | |
| 6,256,541 B1 | 7/2001 | Heil et al. | |
| 6,363,286 B1 | 3/2002 | Zhu et al. | |
| 6,363,287 B1 | 3/2002 | Brabee et al. | |
| 6,445,954 B1 | 9/2002 | Olive et al. | |
| 6,463,323 B1 | 10/2002 | Conrad-Vlasak et al. | |
| 6,501,992 B1 | 12/2002 | Belden et al. | |
| 6,532,378 B2 | 3/2003 | Saksena et al. | |
| 6,643,546 B2 | 11/2003 | Mathis et al. | |
| 6,718,211 B2 | 4/2004 | Smits | |
| 6,741,893 B2 | 5/2004 | Smits | |
| 6,760,619 B1 | 7/2004 | Helland et al. | |
| 6,882,886 B1 | 4/2005 | Witte et al. | |
| 7,238,883 B2 | 7/2007 | Zarembo | |
| 7,392,094 B2 * | 6/2008 | Zhang et al. | 607/126 |
| 7,512,440 B2 | 3/2009 | Ortega et al. | |
| 7,555,351 B2 * | 6/2009 | Zhang et al. | 607/126 |
| 7,890,188 B2 * | 2/2011 | Zhang et al. | 607/122 |
| 2001/0020179 A1 | 9/2001 | Audoglio | |
| 2001/0031987 A1 | 10/2001 | Saksena et al. | |
| 2002/0049485 A1 | 4/2002 | Smits | |
| 2002/0065544 A1 | 5/2002 | Smits | |
| 2004/0054390 A1 | 3/2004 | Zarembo et al. | |
| 2004/0122496 A1 | 6/2004 | Zhang et al. | |
| 2004/0122497 A1 | 6/2004 | Zhang et al. | |
| 2004/0122498 A1 | 6/2004 | Zhang et al. | |
| 2004/0147994 A1 | 7/2004 | Zhang et al. | |
| 2004/0260374 A1 | 12/2004 | Zhang et al. | |
| 2004/0260375 A1 | 12/2004 | Zhang et al. | |
| 2005/0149155 A1 | 7/2005 | Scheiner et al. | |
| 2005/0149156 A1 | 7/2005 | Libbus et al. | |
| 2005/0228469 A1 | 10/2005 | Zarembo et al. | |
| 2006/0089694 A1 | 4/2006 | Zhang et al. | |
| 2007/0205014 A1 | 9/2007 | Zarembo | |
| 2007/0299492 A1 | 12/2007 | Zhang et al. | |
| 2008/0262586 A1 | 10/2008 | Zhang et al. | |
| 2009/0264974 A1 | 10/2009 | Zhang et al. | |

OTHER PUBLICATIONS

U.S. Appl. No. 10/325,659, Decision on Appeal, dated Feb. 26, 2010, 16 pages.
U.S. Appl. No. 10/325,659, Notice of Abandonment dated Oct. 6, 2010, 2 pages.
U.S. Appl. No. 10/352,546, Restriction Requirement dated Nov. 8, 2005, 5 pages.
U.S. Appl. No. 10/352,546, Response to Restriction Requirement Filed Dec. 9, 2005, 8 pages.
U.S. Appl. No. 10/352,546, non-final office action mailed Dec. 23, 2005, 8 pages.
U.S. Appl. No. 10/352,546, Response to Non-Final Office Action filed Mar. 23, 2006, 11 pages.
U.S. Appl. No. 10/352,546, Final Office Action dated Apr. 17, 2006, 10 pages.
U.S. Appl. No. 10/352,546, Response to Final Office Action filed Jun. 27, 2006.
U.S. Appl. No. 10/352,546, Advisory Action mailed Jul. 5, 2006.
U.S. Appl. No. 10/352,546, RCE filed Jul. 17, 2006.
U.S. Appl. No. 10/352,546, Non-Final Office Action filed Oct. 13, 2006.

U.S. Appl. No. 10/352,546, Response to Non-Final Office Action filed Feb. 13, 2007.
U.S. Appl. No. 10/352,546, Final Office Action mailed May 25, 2007.
U.S. Appl. No. 10/352,546, RCE and Amendment filed Jul. 25, 2007.
U.S. Appl. No. 10/352,546, Non-Final Office Action filed Sep. 14, 2007.
U.S. Appl. No. 10/352,546, Response to Non-Final Office Action filed Dec. 14, 2007.
U.S. Appl. No. 10/352,546, Final Office Action mailed Feb. 21, 2008.
U.S. Appl. No. 10/352,546, RCE and Amendment filed May 21, 2008.
U.S. Appl. No. 10/352,546, Examiner Interview Summary filed May 22, 2008.
U.S. Appl. No. 10/352,546, Non-Final Office Action filed Sep. 19, 2008.
U.S. Appl. No. 10/352,546, Examiner Interview Summary filed Jan. 21, 2009.
U.S. Appl. No. 10/352,546, Examiner Interview Summary filed Jan. 26, 2009.
U.S. Appl. No. 10/352,546, Examiner Interview Summary filed Feb. 13, 2009.
U.S. Appl. No. 10/352,546, Response to Non-Final Office Action filed Feb. 19, 2009.
U.S. Appl. No. 10/352,546, Final Office Action mailed Apr. 14, 2009.
U.S. Appl. No. 10/352,546, Examiner Interview Summary filed Aug. 10, 2009.
U.S. Appl. No. 10/352,546, RCE and Amendment filed Oct. 13, 2009.
U.S. Appl. No. 10/352,546, Non-Final Office Action filed Dec. 10, 2009.
U.S. Appl. No. 10/352,546, Response to Non-Final Office Action filed Apr. 1, 2010.
U.S. Appl. No. 10/352,546, Final Office Action mailed Jun. 1, 2010.
U.S. Appl. No. 10/352,546, RCE and Amendment filed Aug. 31, 2010.
U.S. Appl. No. 10/352,546, Restriction Requirement filed Oct. 7, 2010.
U.S. Appl. No. 10/352,546, Response to Restriction Requirement filed Oct. 25, 2010.
U.S. Appl. No. 10/352,546, Non-Final Office Action filed Nov. 26, 2010.
U.S. Appl. No. 10/352,546, Response to Non-Final Office Action filed Feb. 15, 2011.
U.S. Appl. No. 10/352,546, Final Office Action mailed Apr. 6, 2011, 12 pages.
U.S. Appl. No. 12/493,974, Preliminary Amendment filed Jun. 16, 2010, 8 pages.
JP Application No. 2006-503065, Office Action Mailed Sep. 24, 2009, 5 pages.
"U.S. Appl. No. 10/325,433, Advisory Action mailed Jan. 15, 2008", 3 pgs.
"U.S. Appl. No. 10/325,433, Examiner Interview Summary mailed Feb. 21, 2008", 1 pg.
"U.S. Appl. No. 10/325,433, Final Office Action mailed Oct. 26, 2007", 8 pgs.
"U.S. Appl. No. 10/325,433, Non Final Office Action mailed Jun. 1, 2007", 7 pgs.
"U.S. Appl. No. 10/325,433, Non-Final Office Action mailed Jul. 31, 2006", 13 pgs.
"U.S. Appl. No. 10/325,433, Non-Final Office Action mailed Nov. 16, 2005", 8 pgs.
"U.S. Appl. No. 10/325,433, Notice of Allowance mailed Feb. 21, 2008", 5 pgs.
"U.S. Appl. No. 10/325,433, Response filed May 16, 2006 to Non-Final Office Action mailed Nov. 16, 2005", 16 pgs.
"U.S. Appl. No. 10/325,433, Response filed Sep. 4, 2007 to Non-Final Office Action mailed Jun. 1, 2007", 15 pgs.
"U.S. Appl. No. 10/325,433, Response filed Nov. 22, 2006 to Non Final Office Action mailed Jul. 31, 2006", 17 pgs.
"U.S. Appl. No. 10/325,433, Response filed Dec. 21, 2007 to Final Office Action mailed Oct. 26, 2007", 16 pgs.
"U.S. Appl. No. 10/325,443, Response filed Jan. 28, 2008 to Advisory Action mailed Jan. 15, 2008", 8 pgs.

"U.S. Appl. No. 10/325,658, Advisory Action mailed Dec. 22, 2008", 3 pgs.
"U.S. Appl. No. 10/325,658, Final Office Action mailed Jan. 19, 2010", 8 pgs.
"U.S. Appl. No. 10/325,658, Final Office Action mailed Oct. 15, 2008", 9 pgs.
"U.S. Appl. No. 10/325,658, Non-Final Office Action mailed Sep. 22, 2009", 6 pgs.
"U.S. Appl. No. 10/325,658, Response filed Mar. 22, 2007 to Final Office Action mailed Dec. 22, 2006 and Advisory Action mailed Mar. 8, 2009", 8 pgs.
"U.S. Appl. No. 10/325,658, Response filed Nov. 21, 2007 to Non-Final Office Action mailed Aug. 23, 2007", 11 pgs.
"U.S. Appl. No. 10/325,658, Response filed Dec. 10, 2009 to Non Final Office Action mailed Sep. 22, 2009", 7 pgs.
"U.S. Appl. No. 10/325,658, Response filed Dec. 15, 2008 to Final Office Action mailed Oct. 15, 2008", 9 pgs.
"U.S. Appl. No. 10/325,658, Non Final Office Action mailed Sep. 22, 2009", 6 pgs.
"U.S. Appl. No. 10/325,658, Response filed Feb. 22, 2008 to Restriction Requirement mailed Jan. 22, 2008", 7 pgs.
"U.S. Appl. No. 10/325,658, Restriction Requirement mailed Jan. 22, 2008", 9 pgs.
"U.S. Appl. No. 10/325,659, Non-Final Office Action mailed Jun. 12, 2007", 8 pgs.
"U.S. Appl. No. 10/325,659, Appeal Brief filed Dec. 3, 2007", 26 pgs.
"U.S. Appl. No. 10/325,659, Appellants' Reply Brief filed Apr. 22, 2008", 5 pgs.
"U.S. Appl. No. 10/325,659, Decision on Pre-Appeal Brief mailed Oct. 31, 2007", 2 pgs.
"U.S. Appl. No. 10/325,659, Examiner Interview Summary mailed Jan. 25, 2006", 1 pg.
"U.S. Appl. No. 10/325,659, Examiner's Answer mailed Feb. 22, 2008", 25 pgs.
"U.S. Appl. No. 10/325,659, Pre-Appeal Brief Request filed Oct. 3, 2007", 5 pgs.
"U.S. Appl. No. 10/895,747, Non-Final Office Action mailed Jul. 5, 2007", 11 pgs.
"U.S. Appl. No. 10/895,747, Advisory Action mailed Mar. 18, 2008", 2 pgs.
"U.S. Appl. No. 10/895,747, Advisory Action mailed Mar. 20, 2007", 3 pgs.
"U.S. Appl. No. 10/895,747, Final Office Action mailed Dec. 19, 2007", 9 pgs.
"U.S. Appl. No. 10/895,747, Final Office Action mailed Dec. 22, 2006", 9 pgs.
"U.S. Appl. No. 10/895,747, Non-Final Office Action mailed Jul. 18, 2006", 11 pgs.
"U.S. Appl. No. 10/895,747, Request for Continued Examination mailed Apr. 23, 2007", 1 pg.
"U.S. Appl. No. 10/895,747, Response filed Feb. 19, 2008 to Final Office Action mailed Dec. 19, 2007", 18 pgs.
"U.S. Appl. No. 10/895,747, Response filed Feb. 22, 2007 to Final Office Action mailed Dec. 22, 2006", 18 pgs.
"U.S. Appl. No. 10/895,747, Response filed Oct. 5, 2007 to Non-Final Office Action mailed Jul. 5, 2007", 17 pgs.
"U.S. Appl. No. 10/895,747, Response filed Oct. 18, 2006 to Non Final Office Action mailed Jul. 18, 2006", 14 pgs.
"U.S. Appl. No. 10/895,748, Final Office Action mailed Jan. 31, 2008", 10 pgs.
"U.S. Appl. No. 10/895,748, Final Office Action mailed Mar. 28, 2007", 9 pgs.
"U.S. Appl. No. 10/895,748, Final Office Action mailed Nov. 19, 2008", 9 pgs.
"U.S. Appl. No. 10/895,748, Non Final Office Action mailed Sep. 25, 2006", 9 pgs.
"U.S. Appl. No. 10/895,748, Non-Final Office Action mailed May 16, 2008", 11 pgs.
"U.S. Appl. No. 10/895,748, Notice of Allowance mailed Feb. 27, 2009", 6 pgs.
"U.S. Appl. No. 10/895,748, Response filed Jan. 21, 2009 to Final Office Action mailed Nov. 19, 2008", 8 pgs.

"U.S. Appl. No. 10/895,748, Response filed Mar. 31, 2008 to Final Office Action mailed Jan. 31, 2008", 12 pgs.

"U.S. Appl. No. 10/895,748, Response filed May 29, 2007 to Final Office Action mailed Mar. 28, 2007", 13 pgs.

"U.S. Appl. No. 10/895,748, Response filed Aug. 15, 2008 to Non-Final Office Action mailed May 16, 2008", 13 pgs.

"U.S. Appl. No. 10/895,748, Response filed Sep. 12, 2007 to Non-Final Office Action mailed Jun. 12, 2007", 12 pgs.

"U.S. Appl. No. 10/895,748, Response filed Dec. 22, 2006 to Non-Final Office Action mailed Sep. 25, 2006", 13 pgs.

"U.S. Appl. No. 11/895,808, Response filed Apr. 24, 2009 to Restriction Requirement mailed Mar. 24, 2009", 8 pgs.

"U.S. Appl. No. 11/895,808, Restriction Requirement mailed Mar. 24, 2009", 13 pgs.

Libbus, Imad, "Lead for Stimulating the Baroreceptors in the Pulmonary Artery", U.S. Appl. No. 10/746,861, filed Dec. 24, 2003, 21 pgs.

Scheiner, Avram, "Stimulation Lead for Stimulating the Baroreceptors in the Pulmonary Artery", U.S. Appl. No. 10/746,852, filed Dec. 24, 2003, 25 pgs.

U.S. Appl. No. 10/895,747, Pre Appeal Brief Request mailed Apr. 21, 2008, 5 pages.

U.S. Appl. No. 10/895,747, Appeal Brief mailed Jul. 2, 2008, 19 pages.

"U.S. Appl. No. 10/325,433 Notice of Allowance mailed May 3, 2007", 9 pgs.

"U.S. Appl. No. 10/325,658 Advisory Action mailed Mar. 8, 2007", 3 pgs.

"U.S. Appl. No. 10/325,658 Advisory Action mailed Apr. 3, 2007", 3 pgs.

"U.S. Appl. No. 10/325,658 Final office action mailed Dec. 22, 2006", 10 pgs.

"U.S. Appl. No. 10/325,658 Non Final office action mailed Jul. 7, 2006", 13 pgs.

"U.S. Appl. No. 10/325,658 Non Final office action mailed Nov. 22, 2005", 20 pgs.

"U.S. Appl. No. 10/325,658 Non Final Office Action mailed Aug. 23, 2007", 11 pgs.

"U.S. Appl. No. 10/325,658 Notice of allowance mailed May 3, 2007", 9 pgs.

"U.S. Appl. No. 10/325,658 Response filed Feb. 22, 2007 to Final office action mailed Dec. 22, 2006", 23 pgs.

"U.S. Appl. No. 10/325,658 Response filed Apr. 23, 2007 to Advisory Action mailed Apr. 3, 2007", 8 pgs.

"U.S. Appl. No. 10/325,658 Response filed May 18, 2006 to Non Final office action mailed Nov. 22, 2005", 24 pgs.

"U.S. Appl. No. 10/325,658 Response filed Oct. 10, 2006 to Non Final office action mailed Jul. 7, 2006", 20 pgs.

"U.S. Appl. No. 10/325,659 Advisory Action mailed Jul. 23, 2007", 3 pgs.

"U.S. Appl. No. 10/325,659 Final Office Action mailed May 3, 2007", 17 pgs.

"U.S. Appl. No. 10/325,659 Non Final Office Action mailed Jun. 1, 2007", 9 pgs.

"U.S. Appl. No. 10/325,659 Non-Final Office Action mailed Jan. 25, 2006", 14 pgs.

"U.S. Appl. No. 10/325,659 Non-Final Office Action mailed Aug. 4, 2006", 14 pgs.

"U.S. Appl. No. 10/325,659 Non-Final Office Action mailed Aug. 9, 2005", 16 pgs.

"U.S. Appl. No. 10/325,659 Response filed Dec. 9, 2005 to Non Final Office Action mailed Aug. 9, 2005", 15 pgs.

"U.S. Appl. No. 10/325,659 Response filed May 25, 2006 to Non final office action mailed Jan. 25, 2006", 14 pgs.

"U.S. Appl. No. 10/325,659 Response filed Jul. 3, 2007 to Final office action mailed May 3, 2007", 15 pgs.

"U.S. Appl. No. 10/325,659 Response filed Feb. 5, 2007 to Non final office action mailed Aug. 4, 2007", 13 pgs.

"U.S. Appl. No. 10/895,748 Non Final Office Action mailed Jun. 12, 2007", 8 pgs.

Barin, E. S., et al., "The right ventricular outflow tract as an alternative permanent pacing site: long-term follow-up", *Pacing and Clinical Electrophysiology*, 14(I), (1991), 3-6.

Belham, M., et al., "Pacing Different ventricular site with active and passive fixation leads: comparison of pacing energy requirements", *Pacing and Clinical Electrophysiology*, 21(II), (1999), 977.

Buckingham, T. A., et al., "Right ventricular outflow tract pacing", *Pacing and Electrophysiology*, 20(5 Pt 1), (1997), 1237-42.

Giudici, M., "Comparison of right ventricular outflow tract and apical lead permanent pacing on cardiac output", *American Journal of Cardiology*, 79(2), (1997), 209-212.

Giudici, M C., "Improvement in Cardiac Output with Right Ventricular Outflow Septal Pacing Compare to Apical Pacing is Independent of Pre-existing Conduction Disease", *Pacing and clinical electrophysiology : PACE*, 23(4), (2000), 748.

Giudici, M. C., et al., "Right ventricular outflow tract pacing improves haemodynamics in patients with class III-IV heart failure and existing apical leads", *Pacing and Electrophysiology*, 21(II) Abstract 751, (1998), 2 pgs.

Harris, Z I., et al., "Changes in left ventricular function and dimensions between apical and septal lead position with dual chamber pacing in normally functioning hearts", *Pacing and Clinical Electrophysiology*, 22(II) Abstract, (1999), 751.

Harris, Z. I., et al., "Septal/right ventricular outflow tract (RVOT) lead placement", *Pacing and Electrophysiology*, 22(12), (1999), 1854-1855.

Hirschberg, J., "A New Dual Chamber Single Lead System", *Pacing & Electrophysiology*, 17(11 Pt 2), (Nov. 1994), 1870-1872.

Lubinski, A., et al., "Implantation and follow-up of ICD leads implanted in the right ventricular outflow tract", *Pacing and Electrophysiology*, 23(11 Pt 2), (2000), 1996-98.

Mera, F., et al., "A comparison of ventricular function during high right ventricular septal and apical pacing after his-bundle ablation for refractory atrial fibrillation", *Pacing and Clinical Electrophysiology*, 22(8), (1999), 1234-39.

Rosenqvist, M., "The effect of ventricular activation sequence on cardiac performance during pacing", *Pacing and Electrophysiology*, 19(9), (1996), 1279-1286.

Scherlag, B. J., "Endovascular stimulation within the left pulmonary artery to induce slowing of heart rate and paroxysmal atrial fibrillation.", *Cardiovasc Research*, 54(2), (May 2002), 470-475.

Schwaab, B., et al., "Influence of right ventricular stimulation site on left ventricular function in atrial synchronous ventricular pacing", *Journal of the American College of Cardiology*, 33(2), (1999), 317-23.

Schwaab, B., et al., "Surface ECG guided right ventricular septal lead implantation for the reduction of paced QRS duration", *Pacing and Clinical Electrophysiology*, 22(II), (1999), 806.

Staniewicz, J, et al., "Short versus long term results in right ventricular outflow tract pacing—prospective randomized study", *Pacing and Electrophysiology*, 21(II) Abstract 419, (1998), 2 pgs.

Tang, A.S.L., et al., "Nonthorocotomy implantation of cardioverter defibrillators; preliminary experience with a defibrillation lead paced at the right ventricular outflow tract", *Pacing and Electrophysiology*, 19(6), (1996), 960-964.

Tantengco, M. V., et al., "Left ventricular dysfunction after long-term right ventricular apical pacing in the young", *American Journal of Cardiology*, 37(8), (Jun. 15, 2001), 2093-100.

Tse, Hung-Fat, "Functional abnormalities in patients with permanent right ventricular pacing—The effect of sites of electrical stimulation", *Journal of the American College of Cardiology*, 40(8), (Oct. 16, 2002), 1451-1458.

Victor, F., et al., "Optimal right ventricular pacing site in chronically implanted patients", *Journal of the American College of Cardiology*, 33(2), (1999), 311-6.

Vlay, S. C., et al., "Alternative locations for internal defibrillator electrodes", *Pacing and Clinical Electrophysiology*, 21(6), (1998), 1309-12.

Wolfhard, U. F., et al., "Alternative lead positioning in the right ventricular outflow tract in transvenous implantation of ICDs", *Pacing and Electrophysiology*, 18(1 Pt 2), (1995), 179-81.

Zhang, Yongxing, "Delivery System and Method for Pulmonary Artery Leads", U.S. Appl. No. 10/970,265, filed Oct. 20, 2004, 21 pgs.

* cited by examiner

US 8,204,606 B2

IMPLANTABLE LEAD FOR SEPTAL PLACEMENT OF PACING ELECTRODES

RELATED APPLICATIONS

This application is a continuation of U.S. patent application Ser. No. 10/325,433, filed on Dec. 19, 2002 now U.S. Pat. No. 7,392,094, which is incorporated herein by reference in its entirety.

FIELD OF THE INVENTION

This invention relates to the field of medical leads, and more specifically to an implantable lead.

BACKGROUND

Leads implanted in or about the heart have been used to reverse certain life threatening arrhythmia, or to stimulate contraction of the heart. Electrical energy is applied to the heart via the leads to return the heart to normal rhythm. Leads have also been used to sense in the atrium or ventricle of the heart and to deliver pacing and defibrillation pulses to the atrium or ventricle.

Permanent transvenous pacing is performed using a lead positioned within one or more chambers of the heart. One or more leads may be positioned in the ventricle or in the atrium through a subclavian vein, and the lead terminal pins are attached to a pacemaker which is implanted subcutaneously. One approach to heart pacing is to place an electrode in the apex of the right ventricle. The lead is held in place either passively or actively using a helix, for example.

Another approach is to place the electrode against the high ventricular septum or outflow tract. However, current leads require a lead placed with the electrode in such a position to be actively fixated. This possibly may result in trauma to the heart from cyclical heart motion, micro-dislodgement, and relatively higher pacing thresholds.

SUMMARY

A lead body configured into a preformed J-shape. The lead includes a pacing electrode coupled to an intermediate portion of the lead body located distally from a bottom of the pre-formed J-shape. The lead is adapted to be placed within a heart in a J-shaped configuration with the electrode positioned against a ventricular septum or a right ventricular outflow tract such that at least a portion of the distal end of the lead body is located within a pulmonary artery. In one embodiment, the distal end of the lead is configured to be passively fixated within the pulmonary artery.

Another aspect includes a lead body wherein a section of the intermediate portion of the lead body is less stiff than adjacent sections of the lead body. The lead includes a pacing electrode coupled to the intermediate portion of the lead body and located distally from the less stiff section. The lead is adapted to be placed within a heart in a J-shaped configuration with the less stiff section near a bottom of the J-shape such that the electrode is positioned proximate a ventricular septum or a right ventricular outflow tract and at least a portion of the distal end of the lead body is fixated within a pulmonary artery.

Another aspect includes a method including inserting the lead through a right ventricle and into a pulmonary artery such that the pacing electrode is proximate a ventricular septum or a ventricular outflow tract and the distal end is within the pulmonary artery.

One or more embodiments of the methods and apparatus disclosed herein can result in lower pacing thresholds, better electrode contact, prevent micro-dislodgement of pacing/sensing electrodes, offer better reliability, and ease of implanting and explanting the lead.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
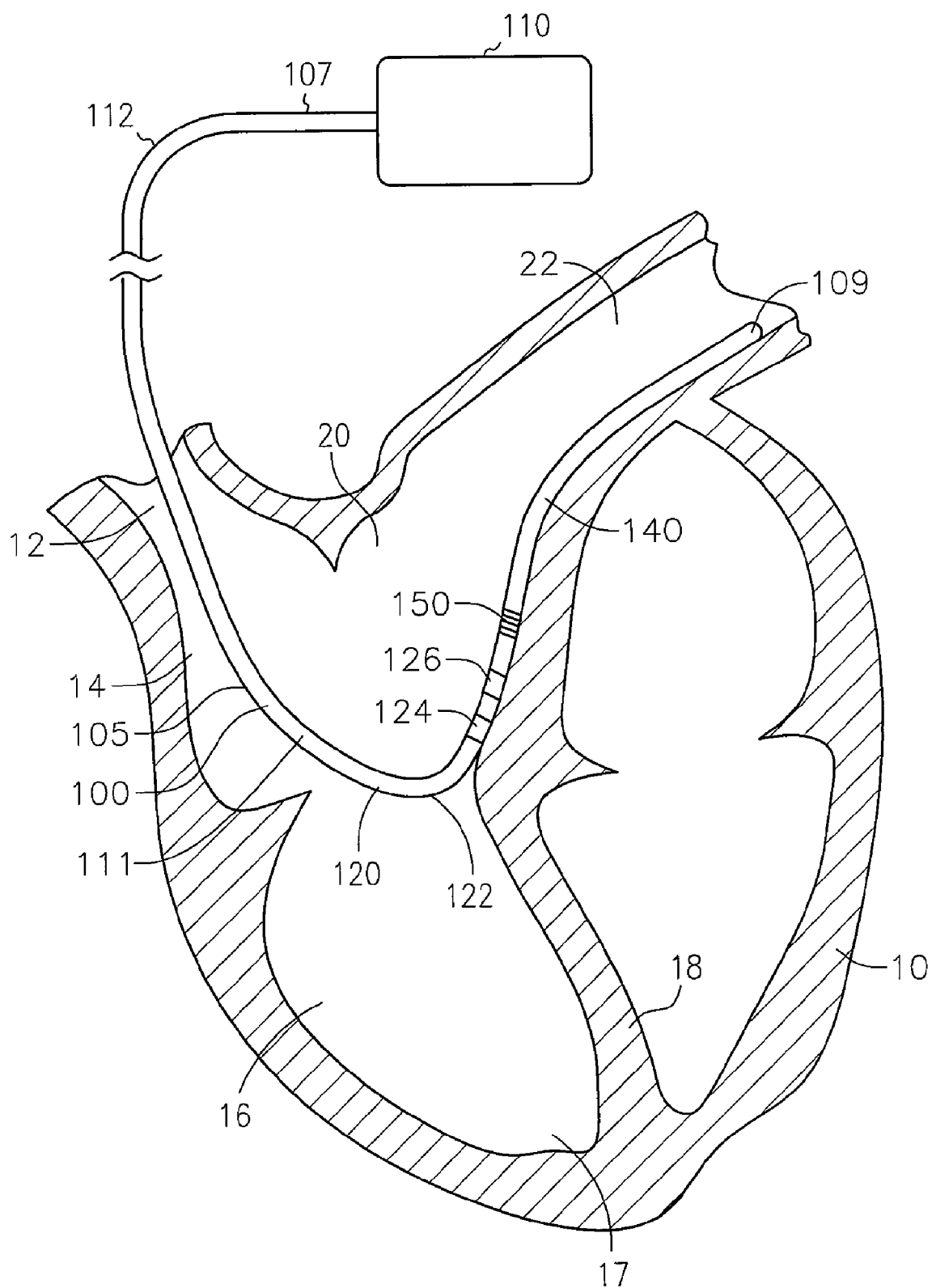
FIG. 1 shows a view of a lead, according to one embodiment, implanted within a heart.

FIG. 1 shows a view of a lead 100 implanted within a heart 10. Heart 10 generally includes a superior vena cava 12, a right atrium 14, a right ventricle 16, a right ventricular apex 17, a ventricular septum 18, and a ventricular outflow tract 20, which leads to a pulmonary artery 22. In one embodiment, lead 100 is adapted to deliver pacing pulses to heart 10. Lead 100 is part of an implantable system including a pulse generator 110.

Pulse generator 110 can be implanted in a surgically-formed pocket in a patient's chest or other desired location. Pulse generator 110 generally includes electronic components to perform signal analysis and processing, and control. Pulse generator 110 can include a power supply such as a battery, a capacitor, and other components housed in a case. The device can include microprocessors to provide processing, evaluation, and to determine and deliver electrical shocks and pulses of different energy levels and timing for ventricular defibrillation, cardioversion, and pacing to heart 10 in response to cardiac arrhythmia including fibrillation, tachycardia, and bradycardia.

In one embodiment, lead 100 is designed for septal placement of the pacing electrode with a distal end of the lead located in the pulmonary artery. Lead 100 can pace and sense at the His bundle/septum/outflow tract, and there is less trauma than caused by active fixation.

In one embodiment, lead 100 includes a lead body 105 extending from a proximal end 107 to a distal end 109 and having an intermediate portion 111. Lead 100 includes one or more conductors, such as coiled conductors, to conduct energy from pulse generator 110 to heart 10, and also to receive signals from the heart. The lead further includes outer insulation 112 to insulate the conductor. The conductors are coupled to one or more electrodes, such as electrodes 124 and 126. Lead terminal pins are attached to pulse generator 110. The system can include a unipolar system with the case acting as an electrode or a bipolar system.

In one embodiment, lead 100 is adapted for septal placement of one or more of the electrodes 124 and 126 while utilizing pulmonary artery 22 for lead fixation. Lead 100 can pace and sense at the interventricular septum 18 or ventricular outflow tract 20. For example, in one embodiment electrodes 124 and 126 are coupled to intermediate portion 111 of the lead. Electrodes 124 and 126 can be pacing/sensing electrodes, such as ring electrodes, designed to deliver a pacing pulse of approximately 0.5 volts at 0.1 milliseconds to approximately 15 volts at 2.0 milliseconds to septum 18 in a bipolar pulsing system. Electrodes 124 and 126 are proximal from distal end 109 and are located on the lead to sense or pace high on the ventricular septum (above apex 17), or in the ventricular outflow tract when the lead is implanted. Advantageously, lead 100 allows such a high placement while not requiring active fixation.

When inserted in the heart and positioned such that electrodes 124 and 126 are against ventricular septum 18, some leads require active fixation. However, active fixation can cause repeated trauma to the endocardial tissue because of the cyclical motion of the heart, and thus may have possible micro-dislodgement and increase defibrillation and pacing thresholds.

In one embodiment, lead body 105 including a preformed, biased J-shape 120 formed in the intermediate portion 111 of the lead body. J-shape 120 is located such that electrode 124 and 126 are located distally from a bottom 122 of the pre-formed J-shape 120. Pre-formed J-shape 120 can be in either 2D or 3D. J-shaped portion 120 of lead 100 allows for better septal/electrode contact. To pre-form the lead, the lead can be manufactured such that it is biased in the J-shape. Thus, the lead naturally reverts to the J-shape when it is implanted. For example, the lead body can be formed in the pre-biased shape or the conductor coils can be formed in the pre-biased shape to bias the lead body into the J-shape. When implanted, the bottom 122 of the J-shape 120 is within the right ventricle 16 and electrodes 124 and 126 are positioned proximate ventricular septum 18 above apex 17, or positioned in right ventricular outflow tract 20 such that at least a portion of the distal end 109 of the lead body is located within a pulmonary artery 22. The pre-formed J-lead design enhances the septal electrode stability and contact. It can help result in low pacing thresholds because of better electrode contacts.

In one embodiment, at least a portion of lead 100 can include an anti-thrombosis coating 140, such as Hypren or polyethleneglycol for example. Coating 140 can be placed on the lead, for example on one or more of the electrodes, or on the distal portion of the lead, or on other segments of the lead.

In one embodiment, lead 100 can include a sensor 150, such as a cardiac output sensor, mounted to the intermediate portion of the lead 100. Sensor 150 can be implanted to such a location within the outflow tract 20 to monitor cardiac output. In one example, cardiac output monitoring sensor 150 can be placed proximate the distal end of the lead to be placed within the pulmonary artery. Sensor 150 can be coupled to pulse generator 110 through a conductor.

In one embodiment, sensor 150 can be a flow speed sensor, allowing the system to know how fast the blood is going through the artery. For example, sensor 150 can be a metal ring, coil, or fin. Such a component would have resistance properties such that if a pulse of energy was sent through the component, the component would heat up, which would in turn increase the electrical resistance of the component. The electrical resistance could be monitored over time to determine how it changes as the blood flow going past it cools it down to blood temperature. The faster the blood flow, the faster the component will cool down and hence the faster the resistance should drop. This cool down or resistance change can be correlated to the blood flow. In other embodiments, sensor 150 can be a pressure sensor. In some embodiments, sensor 150 can include a $CO_2$ or $O_2$ sensor.

In these embodiments, sensor 150 can be used to determine blood flow to allow the position of electrodes 124 and 126 to be optimized. For example, the cardiac output can be used to change the position of the electrode either during or after implantation. Moreover, sensor 150 can be utilized during therapy. For example, if the flow rate goes down the system can deliver a pulse or increase the voltage of the pulse.

In some embodiments, lead 100 can be configured to allow both a stylet or catheter delivery. For example, an opening can be left through the middle of the lead to allow a stylet to be used.

In one embodiment, distal end 109 is adapted for being passively fixated within a pulmonary artery. For example, as will be discussed below, a pre-formed biased distal portion 109 can be provided. In some embodiments, to be discussed below, an active fixation technique is utilized. Some embodiments utilize neither passive nor active fixation, relying on the J-shape 120 and gravity to hold the electrodes 124 and 126 in place against the septum.

Figure 2:
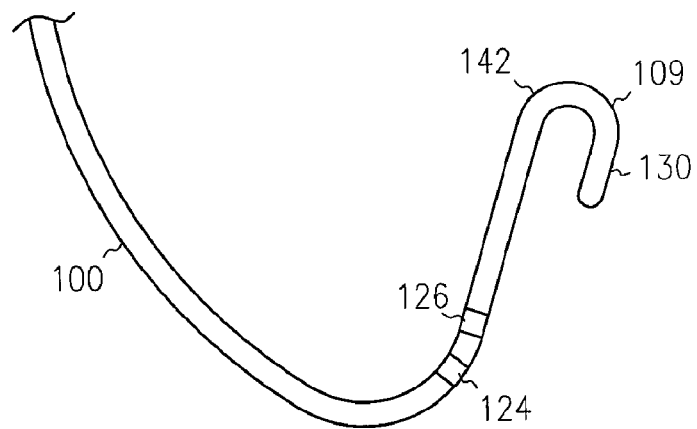
FIG. 2 shows a distal portion of a lead according to one embodiment.

FIG. 2 shows distal portion 109 of lead 100 according to one embodiment. In this example, a pre-formed, biased shape 130 includes a J-shaped curve 142 at a distal tip of the lead body. J-shaped curve 142 can be positioned within pulmonary artery 22 or in one of the branch arteries off of the pulmonary artery to passively fixate the distal end of the lead within the pulmonary artery.

Figure 3:
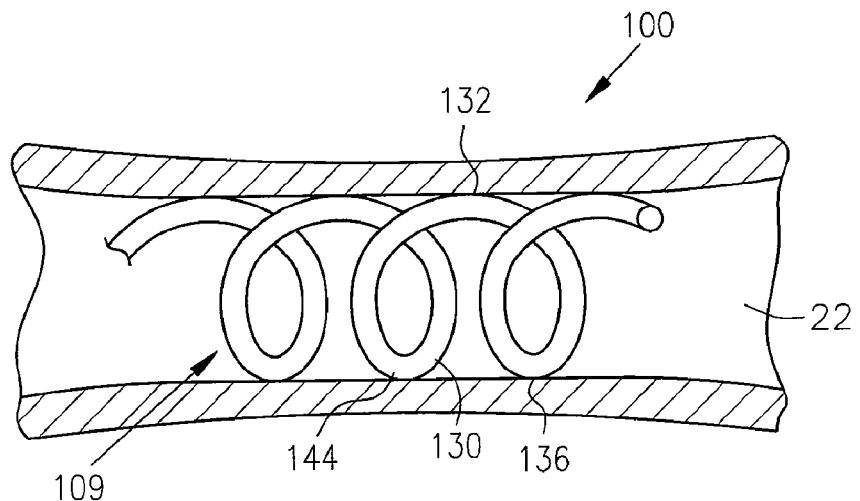
FIG. 3 shows a distal portion of a lead according to one embodiment.

FIG. 3 shows distal portion 109 of lead 100 according to one embodiment. In this example, pre-formed, biased shape 130 includes a spiral configuration 144. The pre-formed, biased shape generally can include at least two lead surfaces (such as surfaces 132 and 136, for example) which are dimensioned and positionable such that the surfaces 132 and 136 contact opposing walls of the pulmonary artery.

Figure 4:
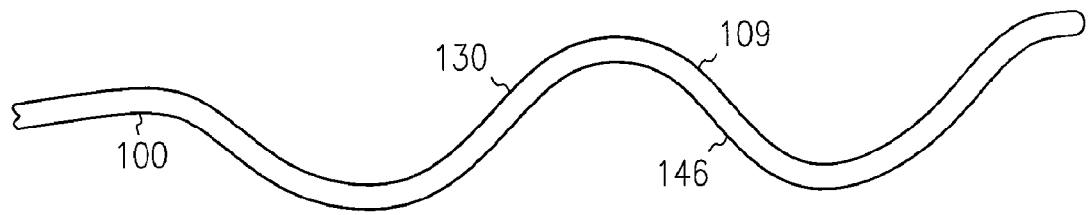
FIG. 4 shows a distal portion of a lead according to one embodiment.

FIG. 4 shows distal portion 109 of lead 100 according to one embodiment. In this example, pre-formed, biased shape 130 includes an S-shaped configuration 146.

In various embodiments, pre-formed bias shape 130 of distal end 109 can include a curved shape such as an S-shape, a C-shape, a J-shape, an O-shape, and other non-linear shapes adapted for contacting one or sides of the pulmonary artery to provide sufficient fixation of the lead. Lead 100 is more reliable because the lead is easier to implant and explant because of the passive fixation which is allowed by the shape of the distal portion of lead 100. For example, passive fixation allows for easier adjustment of electrode placement, and is easier to explant. Moreover, there is less trauma or perforation to endocardium tissue, which can yield lower pacing thresholds. Also, there is less trauma to the septal/outflow tract caused by active fixation at the septal/outflow tract location.

Figure 5:
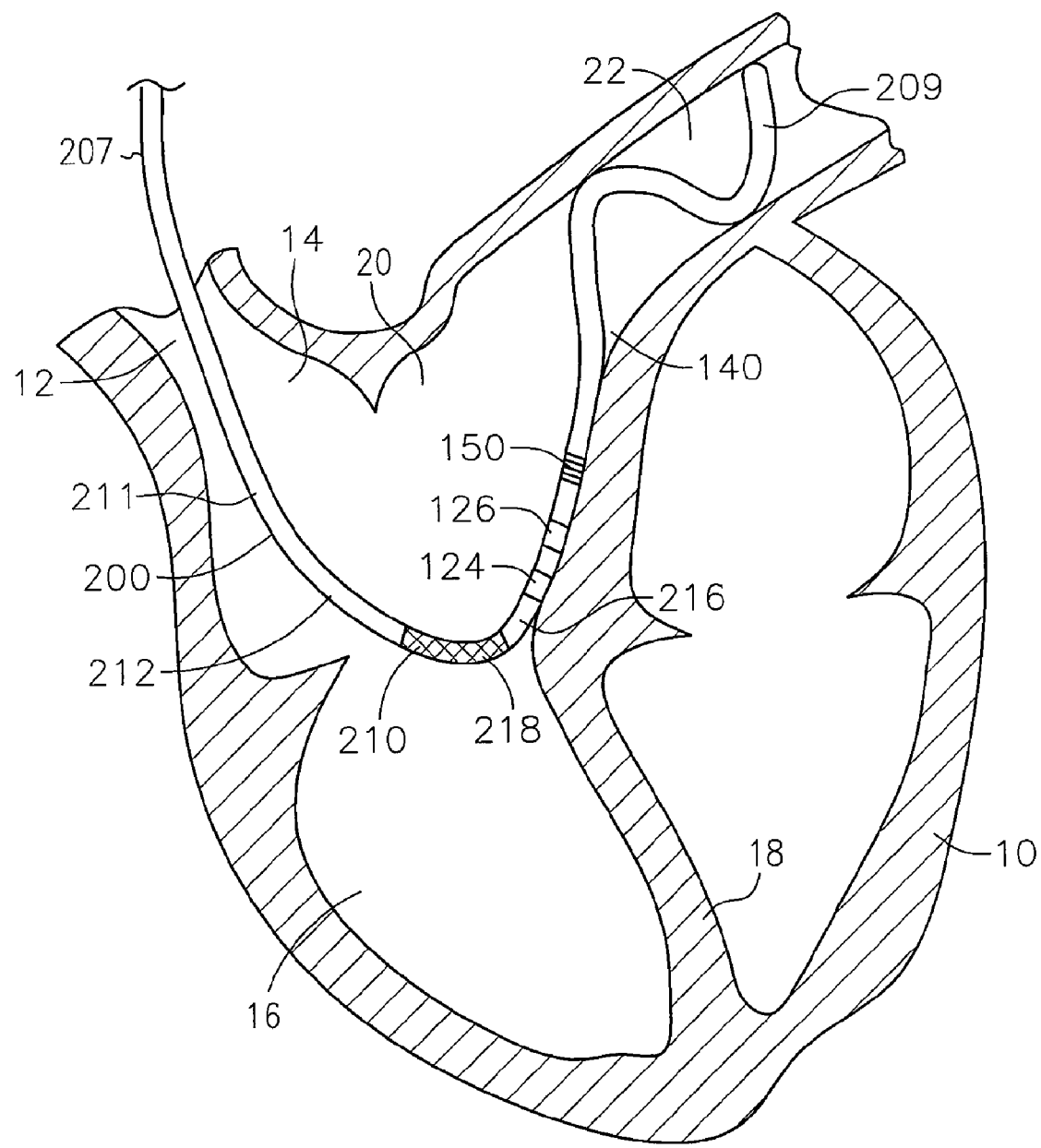
FIG. 5 shows a view of a lead, according to one embodiment, implanted within a heart.

FIG. 5 shows a front view of a lead 200 according to one embodiment. Lead 200 includes some of the components discussed above for lead 100, and the above discussion is incorporated herein. Lead 200 extends from a proximal end 207 to a distal end 209 and includes an intermediate portion 211. Lead 200 can be implanted in heart 10 with distal end 209 located within the pulmonary artery and electrodes 124 and 126 positioned against the septum 18 or within the ventricular outflow tract 20.

In one embodiment, lead 200 includes a section 210 of the intermediate section 211 of the lead which is less stiff than adjacent sections 212 and 216 of the lead body. Lest stiff section 210 is located proximally from electrodes 124 and 126. When lead 200 is positioned in the heart with distal portion 209 in the pulmonary artery, the soft, or less stiff section 210 allows the lead to naturally fall into place and contact the septum due to gravity. Lead 200 is adapted to be placed within a heart in a J-shaped configuration with the less stiff section near a bottom 218 of the J-shape such that electrodes 124 and 126 are positioned proximate ventricular septum 18 or right ventricular outflow tract 20 and at least a portion of the distal end 209 of the lead body is located within a pulmonary artery. The less stiff section 210 provides means on the lead body for reducing any forces caused by heart motion to be transferred to a site of the electrode.

In one embodiment, the less stiff section 210 includes a different, more pliable material than the material of adjacent sections 212 and 216. Again, when the lead is positioned in the heart, the soft segment allows the lead to naturally fall into place and contact the septum due to gravity. The less stiff section 210 enhances the septal electrode stability and contact. Also, it reduces or eliminates the forces and motion (caused by heart motion) transferred to the site of the septal pacing electrodes 124 and 126. This can result in lower pacing thresholds because of better electrode contact.

In this example, as S-shaped passive fixation configuration is provided for distal end 109. In other embodiments, passive techniques as shown above in FIGS. 2-4, or the active technique discussed below can be utilized.

Figure 6:
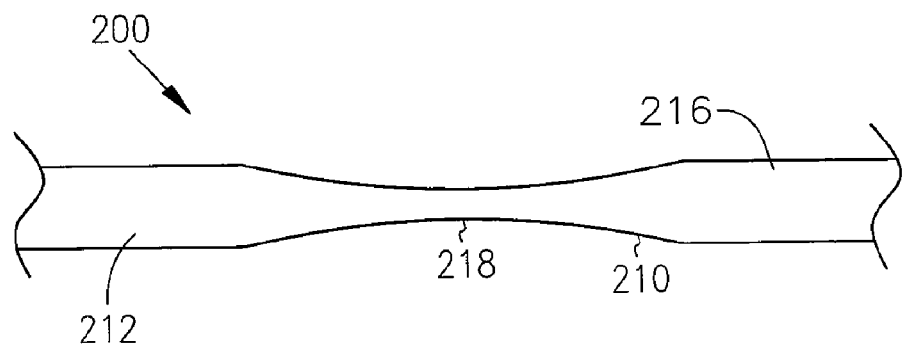
FIG. 6 shows an intermediate portion of a lead according to one embodiment.

FIG. 6 shows a portion of lead 200 according to one embodiment. In one example, less stiff section 210 includes a smaller diameter than the adjacent sections 212 and 216. In other embodiments, less stiff section 210 can be formed by providing a lead wall having a different internal diameter thickness, or by providing a less stiff conductor coil at that location.

In one example use of one or more of the leads discussed herein, the lead is inserted through the right ventricle and into the pulmonary artery using a guiding catheter or a stylet. The lead is positioned until the distal end of the lead is in the pulmonary artery and electrodes are positioned against the septum. The lead can then be fixated there by one of the passive techniques discussed above. When the pulse generator detects a need for pacing, the pulse is delivered via electrodes 124 or 126 in either a bipolar or unipolar system.

Figure 7:
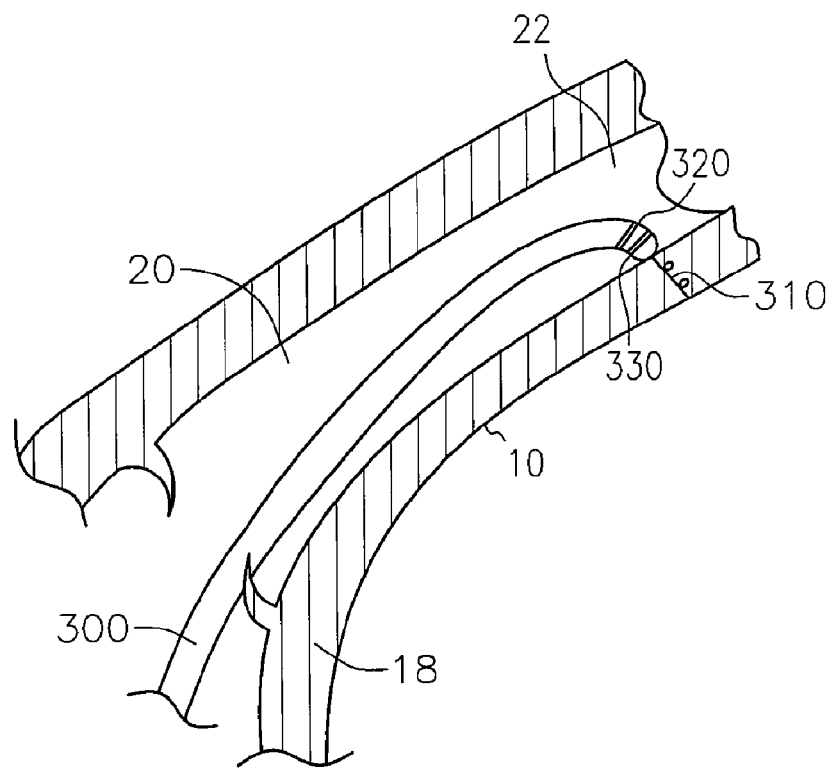
FIG. 7 shows a view of a lead, according to one embodiment, implanted within a heart.

FIG. 7 shows a view of a lead 300 according to one embodiment, implanted within a heart 10. Lead 300 can include one or more of the components discussed above for leads 100 and 200 and the above discussions are incorporated herein. In one embodiment, lead 300 is adapted to be actively fixated within the pulmonary artery 22 utilizing a helix 310, or other active fixation mechanism. In one embodiment, lead 300 includes radiopaque markers 320 near the distal tip to help a physician guide the lead when viewed under fluoroscopy. One embodiment includes a drug elution member 330, which can elude steroids, for example, to reduce inflammatory response of the tissue. In some embodiments, lead 300 does not include either the pre-formed J-shape 120 (FIG. 1) or the less stiff section 210 (FIG. 5) of the leads discussed above. Lead 300 can be an unbiased, flexible lead relying on helix 310 for fixation within the pulmonary artery. In other embodiments, the active fixation technique can be used with the leads discussed above. In some embodiments, active fixation can be provided in addition to or in place of the passive fixation design discussed above.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead comprising:
    a lead body extending from a proximal end to a distal end and having an intermediate portion, wherein the intermediate portion of the lead body is biased to revert to a pre-formed J-shape when implanted;
    the distal end of the lead body including a pre-formed J-shaped fixation curve configured for passive fixation within the pulmonary artery; and
    a pacing electrode coupled to the intermediate portion of the lead body and located distally from a bottom of the pre-formed J-shape, wherein the lead body is configured to be placed within a heart in a J-shaped configuration with the electrode coupled to a ventricular septum or a right ventricular outflow tract and with at least a portion of the distal end of the lead body located within a pulmonary artery.

2. The lead of claim 1, wherein at least a portion of the lead includes an anti-thrombus coating.

3. The lead of claim 1, further comprising a sensor mounted proximate the distal end of the lead body to monitor cardiac output through the pulmonary artery.

4. A lead comprising:
    a lead body extending from a proximal end to a distal end and having an intermediate portion, the distal end including a pre-formed fixation curve configured for being fixated within a pulmonary artery, the pre-formed fixation curve having an S-shaped configuration, a J-shaped configuration or a spiral shaped configuration, and wherein the intermediate portion of the lead body is biased to revert to a pre-formed J-shape when implanted; and
    a pacing electrode mounted to the intermediate portion of the lead body, wherein a base of the J-shaped lead body is proximally located relative to the electrode such that the electrode contacts a ventricular septum when the lead is positioned in a heart with the intermediate section within the right ventricle and the distal end fixated within the pulmonary artery.

5. The lead of claim 4, further comprising a sensor mounted to the lead body to monitor cardiac output.

6. A lead comprising:
    a lead body extending from a proximal end to a distal end and having an intermediate portion with a stiffness less than the proximal and distal ends, wherein the intermediate portion of the lead body is biased to revert to a pre-formed J-shape when implanted; and
    a pacing electrode coupled to the intermediate portion of the lead body and located distally from a bottom of the pre-formed J-shape, wherein the lead body is configured to be placed within a heart in a J-shaped configuration with the electrode coupled to a ventricular septum or a right ventricular outflow tract and with at least a portion of the distal end of the lead body located within a pulmonary artery;
    wherein the distal end of the lead body includes a pre-formed, biased distal tip configured for passively fixating the distal end of the lead body within a pulmonary artery, the pre-formed, biased distal tip including an S-shaped configuration, a J-shaped configuration or a spiral shaped configuration.

* * * * *